United States Patent
Gutfleisch

(10) Patent No.: US 8,642,979 B2
(45) Date of Patent: Feb. 4, 2014

(54) RADIOTHERAPY DEVICE AND METHOD FOR BALANCING A RADIOTHERAPY DEVICE

(75) Inventor: Marcus Gutfleisch, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 360 days.

(21) Appl. No.: 13/173,758

(22) Filed: Jun. 30, 2011

(65) Prior Publication Data
US 2012/0168646 A1 Jul. 5, 2012

(30) Foreign Application Priority Data
Jul. 7, 2010 (DE) .......................... 10 2010 026 375

(51) Int. Cl.
*A61N 5/00* (2006.01)
*G21G 5/00* (2006.01)

(52) U.S. Cl.
USPC .................. 250/492.1; 250/491.1; 250/492.2; 250/396 R; 250/396 ML; 378/15; 378/62; 378/65; 378/162

(58) Field of Classification Search
USPC ..... 250/491.1, 492.1, 492.3, 396 R, 396 ML; 378/15, 62, 65, 162
See application file for complete search history.

(56) References Cited

U.S. PATENT DOCUMENTS

| 4,112,306 A * | 9/1978 | Nunan ......................... 376/112 |
| 4,705,955 A * | 11/1987 | Mileikowsky ............. 250/492.1 |
| 5,047,641 A | 9/1991 | Besseling et al. |
| 6,748,806 B2 | 6/2004 | Halsmer |
| 6,969,194 B1 * | 11/2005 | Nafstadius ..................... 378/197 |
| 2003/0159508 A1* | 8/2003 | Halsmer .......................... 73/462 |
| 2005/0013403 A1 | 1/2005 | Reznicek et al. |

FOREIGN PATENT DOCUMENTS

DE 10 2004 004 300 A1 8/2005
DE 103 20 974 B4 12/2005

OTHER PUBLICATIONS

German Office Action dated Feb. 11, 2011 for corresponding German Patent Application No. DE 10 2010 026 375.3-54 with English translation.
S. Reimoser, "Development and Engineering Design of a Novel Exocentric Carbon-Ion Gantry for Cancer Therapy (The "Riesenrad" Gantry)", Dissertation (Phd-Thesis), pp. 79-82, 2000.

* cited by examiner

*Primary Examiner* — Jack Berman
*Assistant Examiner* — Meenakshi Sahu
(74) *Attorney, Agent, or Firm* — Lempia Summerfield Katz LLC

(57) ABSTRACT

A radiotherapy device having a gantry rotatably mounted to the radiotherapy device with a bearing and a counterweight attached to the gantry. The counterweight has a spatial position relative to the gantry. The spatial position of the counterweight is movable. The device is configured to generate a compensating torque on the bearing, the compensating torque based on a movement of the spatial position of the counterweight, to balance the gantry.

21 Claims, 4 Drawing Sheets

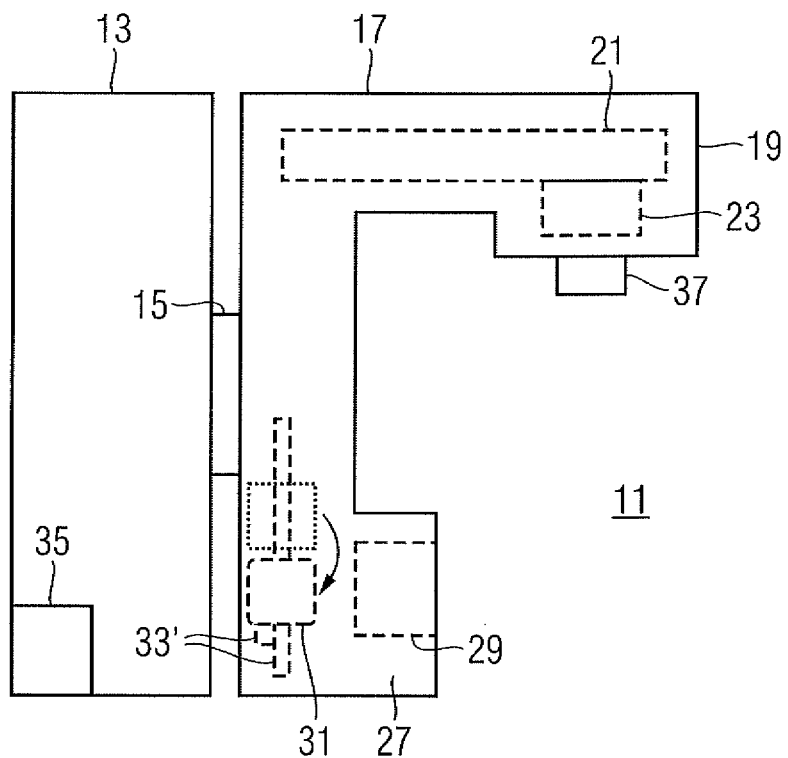
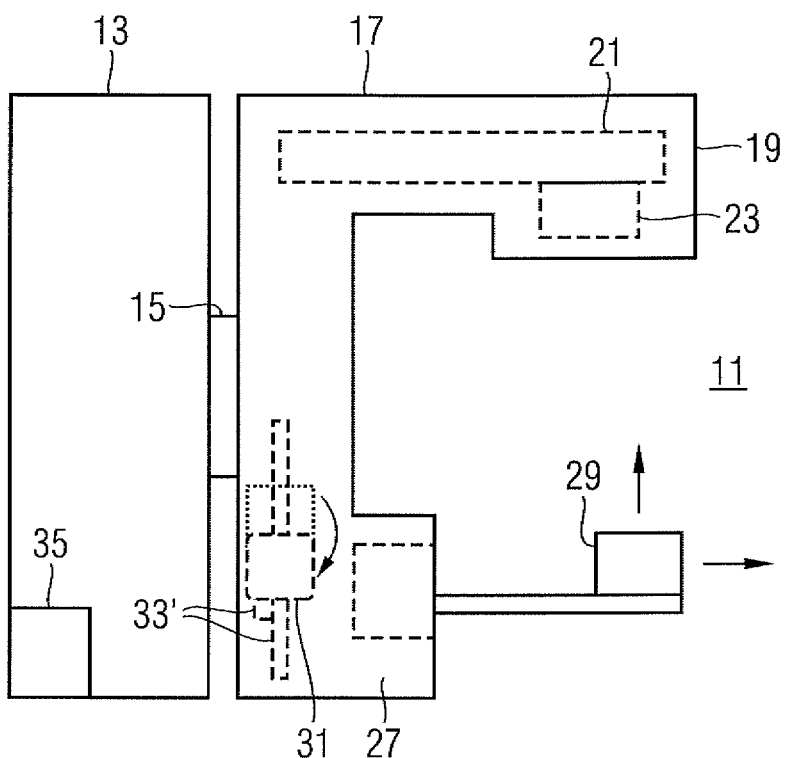

RADIOTHERAPY DEVICE AND METHOD FOR BALANCING A RADIOTHERAPY DEVICE

This application claims the benefit of DE 10 2010 026 375.3, filed Jul. 7, 2010.

BACKGROUND

The present embodiments relate to a radiotherapy device for irradiating tumors and to a method for balancing a radiotherapy device.

Radiotherapy devices irradiate tumors with radiation, such as, with X-ray radiation or electron radiation. Known radiotherapy devices include a rotatable gantry. Using the rotatable gantry, the radiation source may be moved around a patient so that the therapeutic radiation may be directed onto the patient from different spatial directions.

Rotatable gantries may support a plurality of components, such as, for example, components used for beam generation (e.g., particle accelerators) or beam shaping (e.g., collimators and screens). Some of these components may have a considerable intrinsic weight. Accordingly, the gantry may also have a corresponding support structure, which itself has an intrinsic weight, in order to achieve the necessary stability. When the gantry is rotated, large masses weighing, for example, several tons may be moved around the patient.

SUMMARY AND DESCRIPTION

The present embodiments may obviate one or more of the drawbacks or limitations in the related art. For example, a radiotherapy device that permits precise gantry movement around the patient and/or that minimizes the load on the radiotherapy device during rotation of the gantry may be provided. Furthermore, a method for balancing a radiotherapy device that permits precise gantry movement around the patient and/or minimizes the load on the radiotherapy device during rotation of the gantry may be provided.

In the present embodiments, the radiotherapy device has a gantry that is rotatably mounted to the radiotherapy device with the aid of a bearing. The gantry comprises a counterweight, the spatial position of which may, relative to the gantry, be changed. By adjusting the spatial position of the counterweight, a compensating torque may be generated. The generated torque acts on the bearing and, in turn, balances the gantry.

In radiotherapy devices, it is known that the configuration of the gantry may be changed during operation. Such changes in the configuration of the gantry induce a change in the torque that acts on the bearing. To compensate for these torques and balance the gantry, a counterweight is attached to the gantry in a fixed position. Such an arrangement may not, however, account for the flexibility necessary to operate the gantry. With a fixed counterweight, the gantry may operate in some modes in which the torque provided by the counterweight is simply insufficient. If the gantry is then rotated, a heavy load may be placed on the bearing of the gantry. In addition, the desired precision may not be achieved during rotation. Safety and accuracy may thus be compromised during operation of the gantry. Equally, the service life of the device may be reduced.

Smaller counterweights may be attached to the gantry in a spatially fixed position. This may serve to improve or fine-tune the balance of the gantry in some configurations, but only partially resolves these above-noted problems.

In the present embodiments, at least one counterweight may be attached to the gantry such that its spatial position, relative to the gantry, may be changed. By changing the spatial position of the counterweight, the device may generate a compensating torque that acts on the bearing of the gantry. In operation, the spatial position of the counterweight is set such that the compensating torque balances the gantry. As a result, the gantry may be balanced in a flexible manner that is adapted to the individual circumstances, which may be, for example, production-related. Balancing may easily be performed afresh during the operation of the gantry.

The gantry in the present embodiments may be operable to change the configuration of the gantry. Re-configuration of the gantry may induce or produce a change in the torques acting on the bearing. The position of the counterweight may be selected or changed such that the compensating torque caused by the change in the position of the counterweight at least largely offsets or compensates for the change in torque induced by the re-configuration of the gantry.

In one embodiment, the counterweight may be movably mounted to the gantry using a relocation mechanism that permits or allows a user to manually change the position of the counterweight. Accordingly, the balancing of the radiotherapy device may be performed manually. Moreover, the balancing may be easily adapted and/or reset during operation of the radiotherapy device. For example, it may be desirable to reset the balancing of the device during periodically performed maintenance work. As a result, a user may check whether the balancing is still sufficient. If the balancing has to be recalibrated, the user may easily change the position of the counterweight by exerting a direct force on the relocation mechanism.

In another embodiment, the counterweight may be movably mounted to the gantry with a relocation mechanism such that the position of the counterweight may be changed using a motor of the relocation mechanism. In contrast to the embodiment in which the position of the counterweight may be manually changed, this embodiment may allow the counterweight to be re-positioned, in a motor-powered fashion, in a convenient manner. A motor-powered positional change of the counterweight may also be performed if the counterweight is arranged completely behind a cover of the gantry and is not arranged so as to be readily accessible from the outside.

In one embodiment, the relocation mechanism may utilize a control device to automatically control and change the position of the counterweight. This, for example, may enable the balancing to be controlled and adapted even during operation. Depending on the configuration of the gantry, the control device may automatically change the spatial position of the counterweight. Different gantry configurations may, for example, be stored in the control device. Based on which gantry configuration is selected or is being used, the control device may automatically set the position of the counterweight. As a result, the control device may ensure that the gantry is as optimally balanced as possible at all times. This minimizes a load on the bearing of the gantry caused by torques acting on the bearing. The spatial position of the externally controlled counterweight may be monitored and verified by the control device.

In one embodiment, the gantry may be rotated using a rotation mechanism and the control device may be operable to set a position of the counterweight using or according to a load on the rotation mechanism. Setting position based on the load may be advantageous, since it may be necessary to adjust the balancing of the gantry for various unpredictable reasons during operation of the radiotherapy device. Since the load on the rotation mechanism may be determined or measured during operation, the position of the counterweight and thus the balance of the gantry may be quickly and easily adjusted.

In one embodiment, the rotation mechanism may comprise a motor for rotating the gantry. The control device may be designed to control the position of the counterweight using a motor current input from the motor during rotation of the gantry. If, for example, it is established that the motor current input during a clockwise revolution of the gantry differs significantly from the motor current input during a counterclockwise revolution of the gantry, this may be an indication that the gantry is no longer sufficiently balanced. The position of the counterweight may be changed until the motor current inputs during clockwise and/or counterclockwise rotation are aligned with each other.

A method for balancing a gantry rotatably mounted to a radiotherapy device may comprise the following acts: (1) positioning a counterweight on the gantry, (2) changing or setting the spatial position of the counterweight, relative to the gantry, using a relocation mechanism, and (3) generating a compensating torque to balance the gantry, the compensating torque generated as a function of the change in the spatial position of the counterweight.

In one embodiment, when the configuration of the gantry is changed and a change in the torque acting on a bearing of the gantry is induced, the spatial position of the counterweight is set such that the change in torque induced by the change in configuration is at least partially offset or compensated for. Such a setting may, in one embodiment, be controlled automatically.

In one embodiment, the spatial position of the counterweight may be set according to the following acts: (1) the gantry is rotated with the aid of a rotation mechanism, (2) a load on the rotation mechanism is determinedvia, for example, a motor current input, and (3) the spatial position of the counterweight is determined using the load on the rotation mechanism. The motor current input of the rotation motor of the gantry may be used to characterize the load on the rotation mechanism and to determine or establish whether the gantry is balanced. The balance of the gantry is then readjusted with the aid of the counterweight.

BRIEF DESCRIPTION OF THE DRAWINGS

FIG. 3 shows a side view of one embodiment of a radiotherapy device with a changed gantry configuration.

FIG. 4 shows a side view of another embodiment of a radiotherapy device with another type of changed gantry configuration.

DETAILED DESCRIPTION OF THE DRAWINGS

Figure 1:
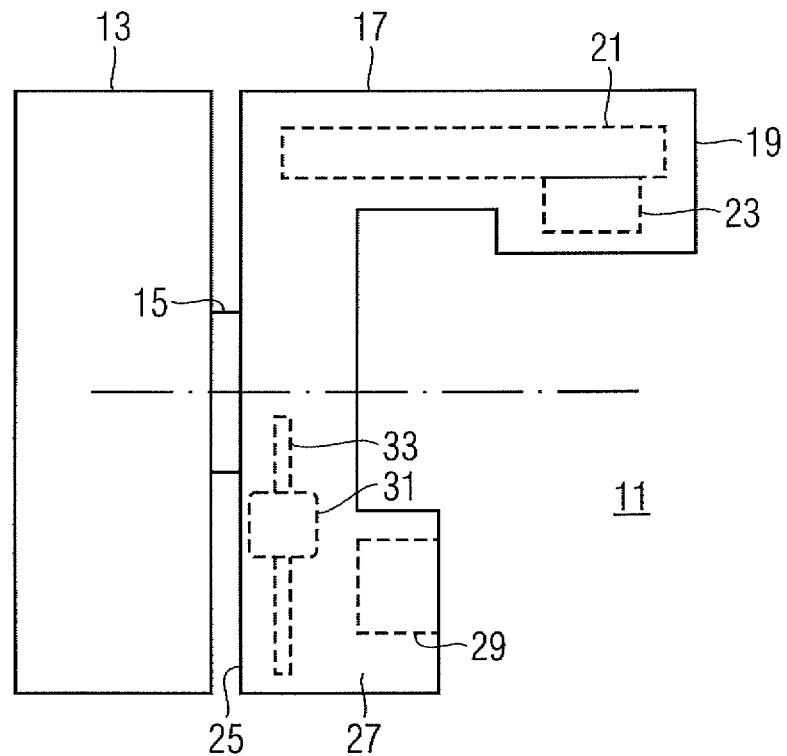
FIG. 1 shows a side view of one embodiment of a radiotherapy device with a gantry having a projecting arm.

FIG. 1 shows a radiotherapy device 11. The radiotherapy device 11 has a stand 13 on which a rotatably mounted gantry 17 is arranged via a bearing 15. With the aid of rotation mechanism (not depicted herein), which comprises a rotation motor, the gantry 17 may be rotated 360° about the bearing 15 and a horizontal axis through the bearing 15.

The gantry 17 has a projecting arm 19. The projecting arm 19 includes components of an accelerator 21 used for beam generation and components of a collimator 23 used for beam shaping and limiting.

Opposite the projecting arm 19, on the other side of the bearing 15, is a counter-arm 25 with a counterweight 27. The counterweight 27 partially offsets or compensates for the torque, caused by the projecting arm 19, that acts on the bearing 15.

The gantry 17 may further include imaging components 29 arranged in the counter-arm 25. The imaging components 29 may include, for example, a radiation source for diagnostic x-ray radiation, and detectors for portal images (EPID), etc.

Inside the housing of the gantry 17 is a counterweight 31 in the counter-arm 25. With the aid of a relocation mechanism 33, the counterweight 31 is movably mounted. The relocation mechanism 33 shown in FIG. 1 is designed as a mechanical relocation mechanism 33 that may allow a user to manually change the distance between the counterweight 31 and the bearing 15. By moving the counterweight 31, the balancing of the gantry 17 may be fine-tuned or adjusted.

In one embodiment, two or more counterweights may each be movably mounted with a relocation mechanism. The counterweights may be arranged symmetrically with respect to a center axis. For example, two counterweights may be arranged symmetrically with respect to a plane that is perpendicular to the plane of rotation of the gantry 25 and in which the central axis of the therapy beam of the radiotherapy device lies.

Figure 7:
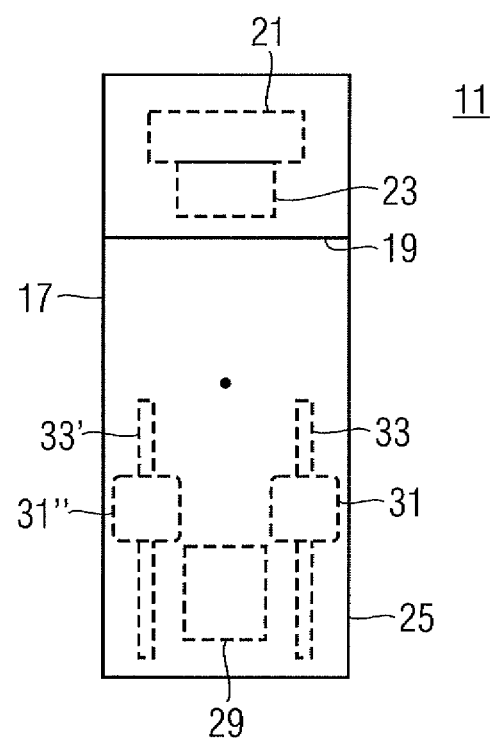
FIG. 7 shows a front view of one embodiment of a radiotherapy device with two counterweights.

As shown in FIG. 1, the two counterweights 31, 31", together with relocation mechanisms 33, 33", may be arranged one behind the other such that two different counterweights may not be visible. In FIG. 7, however, the two counterweights 31, 31" may be seen.

If, as shown in FIG. 1, the gantry 17 has a projecting arm 19 and a counter-arm 25, the two counterweights 31, 31" may be arranged with relocation mechanisms 33, 33" laterally in the counter-arm 25 or, in other words, on both sides of the counter-arm 25. The space between the two counterweights 31, 31" may be used, for example, to accommodate electronics, circuits and/or lines.

Figure 2:
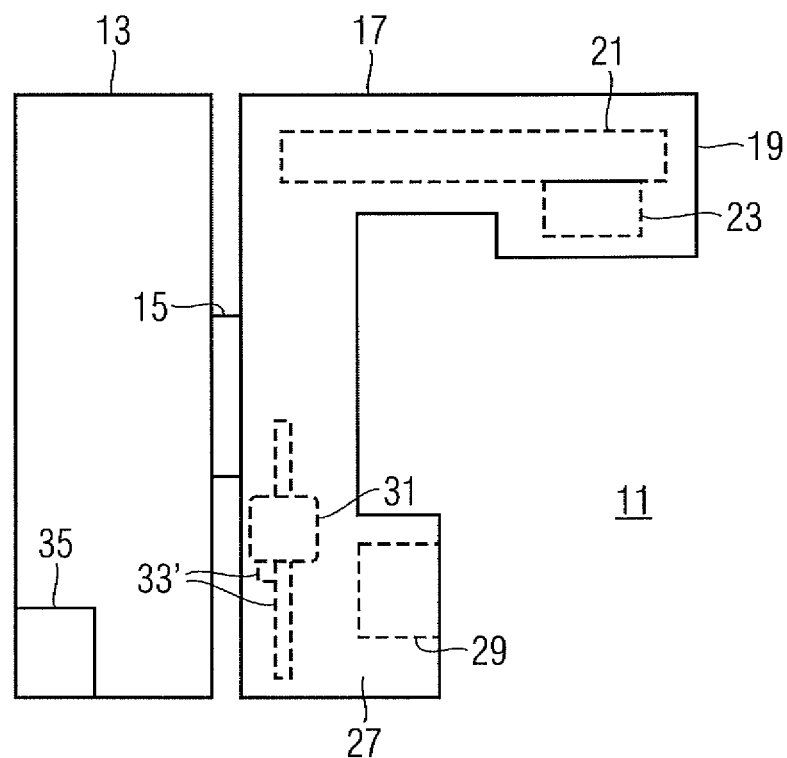
FIG. 2 shows a side view of one embodiment of a radiotherapy device in which a counterweight is controlled and moved in motor-powered fashion.

FIG. 2 shows a modified embodiment of the radiotherapy device 11 shown in FIG. 1. In this embodiment, the relocation mechanism 33' is motor-powered. As a result, the distance between the counterweight 31 and the bearing 15 may be set automatically with a control device 35.

FIG. 3 and FIG. 4 illustrate how balancing of the gantry 17 may be adapted or reset when the configuration changes. FIG. 3 depicts one embodiment in which a mountable attachment 37 is mounted on the projecting arm of the gantry 17. The attachment 37 may, for example, be a further collimation device. Because of the weight of the attachment 37, when a change in the configuration of the gantry 17 occurs it may be necessary to change the balancing of the gantry 17. The gantry 17 may be balanced by changing the position of the counterweight 31. The position of the counterweight 31 may be changed, as shown in FIG. 2, by the control device 35 and the motor-powered relocation mechanism 33'.

In the one embodiment shown in FIG. 4, the configuration of the gantry 17 changes because the imaging component 29 is extended in the counter-arm. This configuration change may be offset or compensated for by, for example, automatically changing the distance between the counterweight 31 and bearing 15 using the control device.

Figure 5:
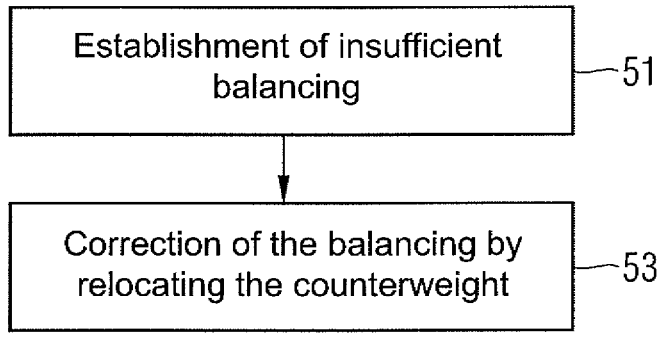
FIG. 5 shows a flowchart of one embodiment of a method for balancing a radiotherapy device.

FIG. 5 shows a flowchart of one embodiment of a method for balancing a gantry. In act 51, an existing balance of the gantry may be changed, and an insufficient balancing of the gantry established, after, for example, the gantry configuration changes.

In act 53, the spatial position of a counterweight is changed, with the aid of a relocation mechanism, to sufficiently balance the gantry.

Figure 6:
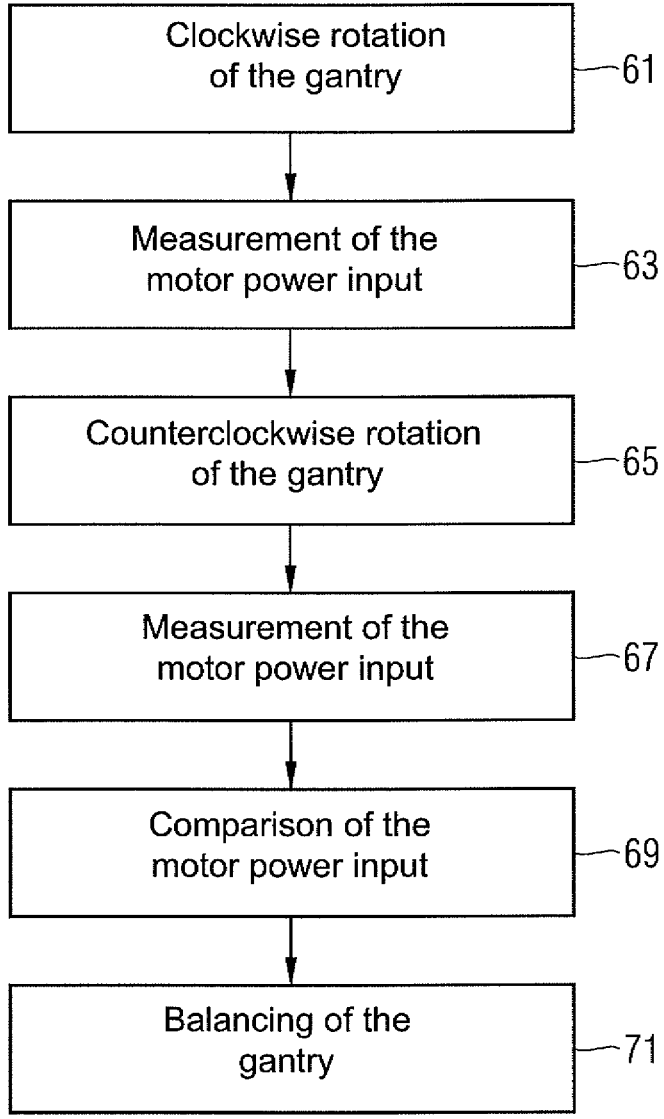
FIG. 6 shows a flowchart of one embodiment of a method for balancing a radiotherapy device.

FIG. 6 shows a flowchart of another embodiment of a method for balancing a gantry. In act 61, the gantry may be rotated by 360°. The starting point for the gantry rotation may, for example, be a position in which the projecting arm is in a vertical position (corresponding to an angular position of 180°). During the clockwise rotation of the gantry, the load current input of the rotation motor may be measured and plotted (act 63) if the projecting arm is in a horizontal position (angular positions 90° and 270°). In act 65, the gantry is rotated 360° in a counterclockwise direction. During the counterclockwise rotation of the gantry, the load current input of the rotation motor is measured and plotted (act 67) if the gantry is in a horizontal position (angular positions 270° and 90°. In act 69, the plotted motor current inputs may be compared to each other.

If, for example, the motor current input when the counter-arm is lifted through the horizontal is less than the motor current input when the counter-arm is lowered through the horizontal, it may be determined that the counterweight of the counter-arm is too light. This may be addressed by positioning the counterweight at a greater distance from the bearing of the gantry (act 71).

After the position of the counterweight has changed, acts 61-69 may be repeated to verify and monitor the correct position of the counterweight.

In the present embodiments, balancing of the gantry may be individually determined and set. The methods described herein may be independent of the absolute value of the motor current input, which, because of bearing resistances that differ from device to device, may turn out differently. The methods described may also be performed if the absolute value of the motor current input changes over the service life of the device.

The invention claimed is:

1. A radiotherapy device comprising:
   a gantry rotatably mounted to the radiotherapy device with a bearing; and
   a counterweight attached to the gantry and having a spatial position relative to the gantry, the spatial position of the counterweight being movable, such that the counterweight causes a compensating torque on the bearing, based on a movement of the spatial position of the counterweight, to balance the gantry.

2. The radiotherapy device as claimed in claim 1, wherein a configuration of the gantry is changeable and wherein a change in configuration induces a change in torque on the bearing when the configuration of the gantry is changed, and
   wherein the change in the torque induced by the change in the configuration is at least partially offset by moving the spatial position of the counterweight.

3. The radiotherapy device as claimed in claim 2, wherein the counterweight is movably mounted to the gantry with a relocation mechanism operable to allow a user to manually change the spatial position of the counterweight.

4. The radiotherapy device as claimed in claim 1, wherein the counterweight is movably mounted to the gantry with a relocation mechanism operable to allow a user to manually change the spatial position of the counterweight.

5. The radiotherapy device as claimed in claim 1, wherein the counterweight is movably mounted to the gantry with a relocation mechanism operable to change the spatial position of the counterweight using a motor.

6. The radiotherapy device as claimed in claim 5, further comprising a control device configured to control the relocation mechanism.

7. The radiotherapy device as claimed in 6, wherein the control device is configured to change the spatial position of the counterweight as a function of a configuration of the gantry.

8. The radiotherapy device as claimed in claim 7, wherein a rotation mechanism is configured to rotate the gantry, and
   wherein the control device is configured to determine the spatial position of the counterweight using a load on the rotation mechanism.

9. The radiotherapy device as claimed in claim 6, wherein a rotation mechanism is configured to rotate the gantry, and
   wherein the control device is configured to determine the spatial position of the counterweight using a load on the rotation mechanism.

10. The radiotherapy device as claimed in claim 8, wherein the rotation mechanism comprises a motor to rotate the gantry, and wherein the control device is configured to control the spatial position of the counterweight using a motor current input of the motor during rotation of the gantry.

11. The radiotherapy device as claimed in claim 2, wherein the counterweight is movably mounted to the gantry with a relocation mechanism operable to change the spatial position of the counterweight using a motor.

12. The radiotherapy device as claimed in claim 11, further comprising a control device configured to control the relocation mechanism.

13. The radiotherapy device as claimed in claim 12, wherein the control device is configured to change the spatial position of the counterweight as a function of a configuration of the gantry.

14. The radiotherapy device as claimed in claim 3, wherein the counterweight is movably mounted to the gantry with a relocation mechanism operable to change the spatial position of the counterweight using a motor.

15. The radiotherapy device as claimed in claim 14, further comprising a control device configured to control the relocation mechanism.

16. The radiotherapy device as claimed in claim 15, wherein the control device is configured to change the spatial position of the counterweight as a function of a configuration of the gantry.

17. A method for balancing a gantry rotatably mounted to a radiotherapy device, the method comprising:
    positioning a counterweight on the gantry;
    changing a spatial position of the counterweight, relative to the gantry, using a relocation mechanism; and
    generating a compensating torque, as a function of the spatial position of the counterweight, to balance the gantry.

18. The method as claimed in claim 17, further comprising:
    changing a configuration of the gantry;
    inducing a change in torque on a bearing of the gantry based on the changed configuration of the gantry; and
    changing the spatial position of the counterweight to at least partially offset the change in the torque on the bearing.

19. The method as claimed in claim 18, further comprising:
    rotating the gantry with the aid of a rotation mechanism;
    determining a load on the rotation mechanism by measuring a motor current input of the rotating mechanism; and determining the spatial position of the counterweight based upon the load on the rotation mechanism.

20. The method as claimed in claim 17, further comprising:
rotating the gantry with the aid of a rotation mechanism;
determining a load on the rotation mechanism by measuring a motor current input of the rotating mechanism; and
determining the spatial position of the counterweight based upon the load on the rotation mechanism.

21. The method as claimed in claim 17, wherein changing the spatial position of the counterweight comprises changing with a relocation mechanism.

* * * * *